US008030313B2

(12) United States Patent
Kostanski et al.

(10) Patent No.: US 8,030,313 B2
(45) Date of Patent: *Oct. 4, 2011

(54) CONTROLLED RELEASE STERILE INJECTABLE ARIPIPRAZOLE FORMULATION AND METHOD

(75) Inventors: Janusz W. Kostanski, Princeton, NJ (US); Takakuni Matsuda, Tokushima (JP); Manoj Nerurkar, Monmouth Junction, NJ (US); Vijay H. Naringrekar, Princeton, NJ (US)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1001 days.

This patent is subject to a terminal disclaimer.

(21) Appl. No.: 11/979,149

(22) Filed: Oct. 31, 2007

(65) Prior Publication Data

US 2008/0112986 A1    May 15, 2008

Related U.S. Application Data

(63) Continuation of application No. 10/968,482, filed on Oct. 19, 2004, now Pat. No. 7,807,680.

(60) Provisional application No. 60/513,618, filed on Oct. 23, 2003.

(51) Int. Cl.
*A61K 31/497* (2006.01)

(52) U.S. Cl. ............ 514/253.07; 514/253.03; 514/252.1

(58) Field of Classification Search ............. 514/253.07, 514/253.03, 252.1
See application file for complete search history.

(56) References Cited

U.S. PATENT DOCUMENTS

| | | | |
|---|---|---|---|
| 4,352,811 A | 10/1982 | Strupczewski et al. | |
| 4,462,996 A | 7/1984 | Noda et al. | |
| 4,734,416 A | 3/1988 | Banno et al. | |
| 4,804,663 A | 2/1989 | Kennis et al. | |
| 5,006,528 A * | 4/1991 | Oshiro et al. | 514/253.07 |
| 5,314,506 A | 5/1994 | Midler et al. | |
| 5,360,616 A | 11/1994 | Flores et al. | |
| 5,612,346 A | 3/1997 | Mesens et al. | |
| 5,688,801 A | 11/1997 | Mesens et al. | |
| 5,955,422 A | 9/1999 | Lin | |
| 6,165,442 A | 12/2000 | Swaerd-Nordmo et al. | |
| 6,267,989 B1 | 7/2001 | Liversidge et al. | |
| 6,297,231 B1 | 10/2001 | Almarsson et al. | |
| 6,455,526 B1 | 9/2002 | Kohn et al. | |
| 6,482,518 B1 | 11/2002 | Short et al. | |
| 6,495,164 B1 | 12/2002 | Ramstack et al. | |
| 6,544,526 B1 | 4/2003 | Crabb et al. | |
| 6,559,128 B1 | 5/2003 | Hamm et al. | |
| 6,669,963 B1 | 12/2003 | Kampinga | |
| 6,977,257 B2 | 12/2005 | Parab et al. | |
| 6,987,111 B2 | 1/2006 | Greco et al. | |
| 7,115,587 B2 | 10/2006 | Nerurkar et al. | |
| 7,514,072 B1 | 4/2009 | Ehrenreich et al. | |
| 7,541,021 B2 | 6/2009 | Sambuco et al. | |
| 7,550,445 B2 | 6/2009 | Nerurkar et al. | |

| | | |
|---|---|---|
| 7,807,680 B2 | 10/2010 | Kostanski et al. |
| 2004/0209843 A1 | 10/2004 | Inoue et al. |
| 2004/0258757 A1 | 12/2004 | Bosch et al. |
| 2005/0032811 A1 | 2/2005 | Brown |
| 2008/0107745 A1 | 5/2008 | Kostanski et al. |
| 2008/0112985 A1 | 5/2008 | Matsuda et al. |
| 2008/0112986 A1 | 5/2008 | Kostanski et al. |
| 2009/0186903 A1 | 7/2009 | Nerurkar et al. |
| 2009/0274628 A1 | 11/2009 | Ottoboni et al. |

FOREIGN PATENT DOCUMENTS

| | | |
|---|---|---|
| EP | 0 072 662 | 8/1982 |
| EP | 0 941 066 B1 | 9/1999 |
| EP | 1 407 785 | 4/2004 |
| EP | 1675573 B1 | 10/2008 |
| ES | 2084594 | 5/1996 |
| GB | 209551 | 2/1923 |
| GB | 2 095 551 A | 10/1982 |
| JP | 2-191256 | 7/1990 |
| JP | 2-191256 A | 7/1990 |
| JP | 2001 187735 A | 7/2001 |
| JP | 2002 241284 A | 8/2002 |
| JP | 2003 063965 A | 3/2003 |
| JP | 2003212852 | 7/2003 |
| RU | 2 082 401 | 6/1997 |
| RU | 2 104 692 | 2/1998 |
| RU | 2 169 574 | 6/2001 |
| WO | 92/10175 A1 | 6/1992 |
| WO | WO 95/13814 | 5/1995 |
| WO | 95/33488 A1 | 12/1995 |
| WO | WO 99/12549 | 3/1999 |
| WO | 00-35475 A2 | 6/2000 |
| WO | 01/58428 A1 | 8/2001 |
| WO | WO 01/72297 | 10/2001 |
| WO | WO 03/026659 | 9/2002 |
| WO | WO 02/085366 | 10/2002 |
| WO | 03/024426 A1 | 3/2003 |
| WO | WO 03/026659 | 4/2003 |
| WO | WO 2004/006886 | 1/2004 |
| WO | WO 2004/017897 | 3/2004 |
| WO | WO 2004/064752 | 8/2004 |
| WO | WO 2005/016262 | 2/2005 |

OTHER PUBLICATIONS

Garza-Flores et al, *Contraception*, 37(5):471-481 (1988). Garza-Flores et al, *Contraception*, 30(4):371-379 (1984).
Diaz-Sánchez et al, *Contraception*, 35(1):57-68 (1987).
Merck Index 13th, Merck & Co., N.J., U.S.A., 2001, No. 791.
Gennaro R. Alfonso, Remington, Farmacia, 19th Edition Panamericana, Spain, 1988, pp. 2337-2338.
Declaration of Daniel R. Deaver submitted in Alkermes's Japanese Patent Application No. 2006-522614.
Leon Lachman, Ph.D. et al, The Theory and Practice of Industrial Pharmacy, Third Edition, Indian Edition, 1987, pp. 644, 655 and 656.
Arthur H. Kibbe, Ph.D., editor, Handbook of Pharmaceutical Excipients, Third Edition, p. 664.
Declaration Under 37 CFR 1.132 of Stephen E. Zale submitted in U.S. Appl. No. 10/635,221 (Brown).

(Continued)

*Primary Examiner* — Yong Chong
(74) *Attorney, Agent, or Firm* — Sughrue Mion, PLLC

(57) ABSTRACT

A controlled release sterile freeze-dried aripiprazole formulation is provided which is formed of aripiprazole of a desired mean particle size and a vehicle therefor, which upon constitution with water and intramuscular injection releases aripiprazole over a period of at least about one week and up to about eight weeks. A method for preparing the controlled release freeze-dried aripiprazole formulation, and a method for treating schizophrenia employing the above formulation are also provided.

35 Claims, 3 Drawing Sheets

OTHER PUBLICATIONS

Michael J. Akers, Excipient-Drug Interactions in Parenteral Formulations, Journal of Pharmaceutical Sciences, vol. 91, No. 11, pp. 2283-2300 (Nov. 2002).

The British Journal of Radiology, 56, p. 897 (Nov. 1983).

Office Action dated Sep. 24, 2010 on U.S. Appl. No. 11/979,144.

Lieberman, Herbert A. et al, "Pharmaceutical Dosage Forms: Disperse Systems" 2nd Ed., vol. 2, pp. 261-301, New York, 1996.

Lieberman, Herbert A. et al, "Pharmaceutical Dosage Forms: Disperse Systems", vol. 1, pp. 152-163, New York, 1988.

Murata et al, "Pharmaceutics", pp. 98-101, Nankodo Co. Ltd., Japan, 1997.

Office Action dated Nov. 16, 2010 on Japanese Patent Application No. 2006-536693.

Prescribing information for Abilify® (Aripiprazole).

Srinivas K.S., Buchireddy R., Madhusudhan G., Mukkanti K., Srinivasulu P., "Stress Degradation Studies on Aripiprazole and Development of a Validated Stability Indicating LC Method", Chromatographia, vol. 68, pp. 635-640 (2008).

Prescribing information for Kenalog®-10 Injection—triamcinolone acetonide injectable suspension, USP.

Prescribing information for Depo-Provera® Contraceptive Injection—medroxyprogesterone acetate sterile aqueous suspension, 150 mg/mL, USP.

Nakamura, A. and Okada, R., "The coagulation of particles in suspension by freezing-thawing—I. Effect of freezing-thawing conditions and other factors on coagulation", Colloid & Polymer Sci., vol. 254, pp. 718-725 (1976).

Nakamura, A. and Okada, R., "The coagulation of particles in suspension by freezing-thawing—IV. Prevention of coagulation by network or eutectic formation", Colloid & Polymer Sci., vol. 255, pp. 362-367 (1977).

Clausi A.L., Merkley S.A., Carpenter J.F., Randolph T.W., "Inhibition of aggregation of aluminum hydroxide adjuvant during freezing and drying", Journal of Pharmaceutical Science, vol. 97, No. 6, pp. 2049-2061 (2008).

Heller, M.C., Carpenter, J.F. and Randolph, T.W., "Protein formulation and lyophilization cycle design: Prevention of damage due to freeze-concentration induced phase separation," Biotechnology & Bioengineering vol. 63, No. 2, pp. 166-174 (1999).

Franks F., "Freeze-drying of bioproducts: putting principles into practice", European Journal of Pharmaceutics and Biopharmaceutics, vol. 45, pp. 221-229 (1998).

Zapata, M.I., Peck, G.E., Hem, S.L., White, J.L., and Feldkamp, J.R., "Mechanism of freeze-thaw instability of aluminum hydroxycarbonate and magnesium hydroxide gels", Journal of Pharmaceutical Science, vol. 73, No. 1, pp. 3-8 (1984).

Nakamura, A. and Okada, R., "The coagulation of particles in suspension by freezing-thawing—II. Mechanism of coagulation", Colloid & Polymer Science, vol. 254, pp. 497-506 (1976).

Tsapis, N., Dufresne, E.R., Sinha, S.S., Riera, C.S., Hutchinson, J.W., Mahadevan, L., and Weitz, D.A., "Onset of Buckling in Drying Droplets of Colloidal Suspensions", Physics Review Letters, vol. 94, pp. 018302-1 to 018302-4 (2005).

Maa Y.F., Zhao L., Payne L.G., Chen D., "Stabilization of alum-adjuvanted vaccine dry powder formulations: Mechanism and application", Journal of Pharmaceutical Science, vol. 92, pp. 319-332 (2003).

Hirakura Y., Kojima S., Okada A., Yokohama S., Yokota S., "The improved dissolution and prevention of ampoule breakage attained by the introduction of pretreatment into the production process of the lyophilized formulation of recombinant human Interleukin-11 (rhIL-11)", International Journal of Pharmaceutics, vol. 286, Nos. 1-2, pp. 53-67 (2004).

Nakamura, A. and Okada, R., "The coagulation of particles in suspension by freezing-thawing—III. Prevention of coagulation by unfrozen water", Colloid & Polymer Science, vol. 255, pp. 343-356 (1977).

Clausi, A. et al, "Influence of Protein conformation and adjuvant aggregation on the effectiveness of aluminum hydroxide adjuvants in a model alkaline phosphatase vaccine," Journal Pharmaceutical Sciences, vol. 98, pp. 114-121 (2009).

Clausi, A. et al, "Influence of Particle Size and antigen binding on effectiveness of aluminum salt adjuvants in a model lysozyme vaccine," Journal of Pharmaceutical Sciences, vol. 97, pp. 5252-5262 (2008).

Chacon, M. et al, "Stability and freeze-drying of cyclosporine loaded poly(D,L lactide-glycolide) carriers," European Journal of Pharmaceutical Sciences, vol. 8, pp. 99-107 (1999).

Kwok, K. et al, "Strategies for maintaining the particle size of peptide DNA condensates following freeze-drying," International Journal of Pharmaceutics, vol. 203, pp. 81-88 (2000).

Perrin, J., "Freezing of Suspensions," American Journal of Hospital Pharmacy, vol. 36, pp. 1157, 1160 and 1163 (Sep. 1979).

Prescribing information for Center-Al® (Allergenic extracts, Alum Precipitated).

Prescribing information for CellCept® Oral Suspension (Roche).

Prescribing information for Kenalog®-40 Injection (triamcinolone acetonide injectable suspension, USP).

Prescribing information for Megestron® Suspension for injection 150 mg/ml (Organon).

Prescribing information for Novolin® 70/30—insulin human injection, suspension (Novo Nordisk).

Lee et al, "Cryoprotectants for Freeze Drying of Drug Nano-Suspensions: Effect of Freezing Rate", Journal of Pharmaceutical Sciences, vol. 98, No. 12, pp. 4808-4817 (Dec. 2009).

Abdelwahed et al, "Freeze-drying of nanoparticles: Formulation, process and storage considerations", Advanced Drug Delivery Reviews, vol. 58, pp. 1688-1713 (2006).

Chaubal and Popescu, "Conversion of Nanosuspensions into Dry Powders by Spray Drying: A Case Study," Pharmaceutical Research, vol. 25, No. 10, pp. 2302-2308 (Oct. 2008).

Van Eerdenbrugh et al, "Drying of crystalline drug nanosuspensions—The importance of surface hydrophobicity on dissolution behavior upon redispersion", European Journal of Pharmaceutical Sciences, vol. 35, pp. 127-135 (2008).

Nakamura, Akio, Hyomen, vol. 13, No. 1, pp. 1-10, published Jan. 1, 1975.

Remington, The Science and Practice of Pharmacy $19^{th}$ ed., pp. 278-282 (1995).

Encyclopedia of Pharmaceutical Technology, vol. 6, pp. 3601-3602.

Pharmaceutical Dosage Forms: Disperse Systems, vol. 2, p. 189 (1996).

Martin's Physical Pharmacy and Pharmaceutical Sciences, Physical Chemical, p. 504.

Nakagawa, Kazuyuki et al., Derivatives of 3, 4-dihydrocarbostyril as beta-adrenergic blocking agents, J. Med. Chem.; 1974; 17(5) pp. 529-533.

Petigara, R. B. et al., Synthesis and central nervous system depressant activity of new piperazine derivatives, 1, J. Med. Chem, 1968; 11(2) pp. 332-336.

Fielden, Marvel L, et al., Synthesis and central nervous system depressant activity of some 5-(2-substituted alkyl)-2-oxazolidinones, J. Med. Chem.; 1973; 16(10) pp. 1124-1128.

The Pharmacological Basis of Therapeutics (Goodman and Gilam, Ed., 1975); pp. 47-53, 153-197 and 590-623.

Alfonso R. Gennaro, ed., "Remington: The Science and Practice of Pharmacy", $19^{th}$ Edition, Mack Publishing Company 1995, pp. 1668-1671.

European Pharmcopeia 6th Edition, published Jul. 16, 2007, p. 736.

Examination report dated Jan. 8, 2010 for Columbian Patent Application No. 06-36842.

*Pharmaceutical Dosage Forms: Disperse Systems*, vol. 1, pp. 153-163 (1998), Lieberman et al. eds., Marcel Dekker Inc.

*Remington's Pharmaceutical Sciences*, pp. 591-592 (1990), Gennaro et al. eds., Mack Publishing Co.

*Handbook of Pharmaceutical Excipients* (Second Edition), pp. 78-81 (1994), Wade and Waller eds., American Pharmaceutical Association.

*Pharmaceutical Dosage Forms: Disperse Systems*, vol. 2, pp. 261-301 (1996), Lieberman et al. eds., Marcel Dekker Inc.

*Handbook of Pharmaceutical Excipients*, pp. 45-48 (1986), American Pharmaceutical Association.

Nema et al, *PDA J. of Pharm. Sci. & Tech.*, 51(4):166-171 (1997).

Edman., *J. of Aerosol Medicine*, 7:S-3 to S-6 (1994).

Altamura et al, *Drugs*, 63(5):493-512 (2003).

Zuidema et al, *International J. of Pharm.*, 47:1-12 (1988).
Strickley et al, *PDA J. of Pharm. Sci. & Tech.*, 53(6):324-349 (1999).
Akers et al, *J. of Parenteral Science & Technology*, 41(3):88-96 (1987).
Handbook of Pharmaceutical Excipients, American Pharmaceutical Association et al, Publs., pp. v-vi (table of contents) (1986).
"Prostein: Oxendolone Injectable Aqueous Suspension Formulation", Standard Commodity Classification No. of Japan 872499 (Jan. 1992).
Shoji, "Manufacture Technology of Solid Tablet", CMC Publishing Co., Ltd., pp. 138-141 (Mar. 5, 1985).
Midgley et al, *Steroids*, vol. 41, No. 4 (Apr. 1983).
Masuoka et al, *ACTA Endocrinologica*, 92(Suppl. 229):24-35 (1979).
Notice of Opposition dated Jul. 22, 2009 to corresponding European Patent No. 1675573.
Search Report for Georgian Patent Application No. 9360012006 dated Oct. 8, 2009.
Office Action for Taiwanese Patent Application No. 93131836 dated Dec. 16, 2009.
Anne Paavola et al, Controlled release and dura mater permeability of lidocaine and ibuprofen from injectable poloxamer-based gels, Journal of Controlled Release, 1998, vol. 52, pp. 169-178.
Physicians' Desk Reference, Edition 51, 1997, pp. 1010-1011, 1710-1713, 2078-2081.
Depo-Medrol—Methylprednisolone Acetate Injectable Suspension, USP—Product Information, pp. 1-17 (Revised May 2008).
Kenalog—40 Injection—Triamcinolone Acetonide Injectable Suspension, USP—Product Information, pp. 1-20 (Revised Oct. 2006).
Alkermes, Inc.'s Opposition to European Patent No. 1675573 (EP Application No. 04795514.1), pp. 1-13 (Jul. 28, 2009).
Office Action dated Apr. 12, 2011 on Taiwanese Application No. 093131836.
Alkermes Controlled Therapeutics, Inc.'s submission dated Mar. 30, 2011 to the European Patent Office in Alkermes's opposition to Otsuka's Pharmaceutical Co., Ltd.'s European Patent No. 1,675,573.
Otsuka Pharmaceutical Co., Ltd.'s submission dated May 5, 2011 to the European Patent Office in Alkermes's opposition to Otsuka's European Patent No. 1,675,573.
Otsuka Pharmaceutical Co., Ltd.'s response dated Mar. 8, 2010 to Alkermes Controlled Therapeutics, Inc.'s opposition to Otsuka's European Patent No. 1,675,573.
Encyclopedia of Pharmaceutical Technology, edited by James Swarbrick, Third Edition, vol. 3, pp. 1884-1885 (Oct 2006).
Declaration Under 37 CFR 1.132 of Stephen E. Zale submitted in U.S. Appl. No. 10/635,221 (Brown), dated Oct. 13, 2006.
Prescribing information for ABILIFY® (Aripiprazole) (2007).
Prescribing information for KENALOG®-10 Injection—triamcinolone acetonide injectable suspension, USP (Revised Dec. 2007).
Prescribing information for DEPO-PROVERA® Contraceptive Injection—medroxyprogesterone acetate sterile aqueous suspension, 150 mg/mL, USP (Revised May 2006).
Prescribing information for Center-Al® (Allergenic extracts, Alum Precipitated) (Revised Jun. 2002).
Prescribing information for CellCept® Oral Suspension (Roche) (Revised Oct. 2009).
Prescribing information for Kenalog®-40 Injection (triamcinolone acetonide injectable suspension, USP) (Revised Oct. 2006).
Prescribing information for Megestron® Suspension for injection 150 mg/ml (Organon) (Feb. 2005).
Prescribing information for Novolin® 70/30—insulin human injection, suspension (Novo Nordisk) (Revised Jun. 2009).
Encyclopedia of Pharmaceutical Technology, vol. 6, pp. 3601-3602 (2007).
Martin's Physical Pharmacy and Pharmaceutical Sciences, Physical Chemical, p. 504 (2006).

* cited by examiner

CONTROLLED RELEASE STERILE INJECTABLE ARIPIPRAZOLE FORMULATION AND METHOD

CROSS-REFERENCE TO RELATED APPLICATIONS

This application is a Continuation of U.S. application Ser. No. 10/968,482, filed Oct. 19, 2004; now U.S. Pat. No. 7,807,680 which claims a benefit of priority from U.S. Provisional Application No. 60/513,618, filed Oct. 23, 2003; the entire disclosure of each of which are herein incorporated by reference.

FIELD OF THE INVENTION

The present invention relates to a controlled release sterile freeze-dried aripiprazole formulation, an injectable formulation which contains the sterile freeze-dried aripiprazole and which releases aripiprazole over at least a one week period, a method for preparing the above formulation, and a method for treating schizophrenia and related disorders employing the above formulation.

BACKGROUND OF THE INVENTION

U.S. Pat. No. 5,006,528 to Oshiro et al. discloses 7-[(4-phenylpiperazino)-butoxy]carbostyrils, which include aripiprazole, as dopaminergic neurotransmitter antagonists.

Aripiprazole which has the structure

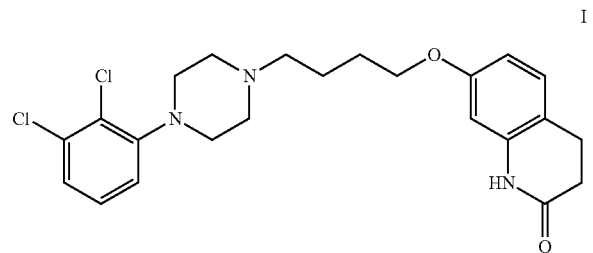

is an atypical antipsychotic agent useful in treating schizophrenia. It has poor aqueous solubility (<1 μg/mL at room temperature).

U.S. Pat. No. 6,267,989 to Liversidge, et al. discloses a method for preventing crystal growth and particle aggregation in nanoparticulate compositions wherein a nanoparticulate composition is reduced to an optimal effective average particle size employing aqueous milling techniques including ball milling.

U.S. Pat. No. 5,314,506 to Midler, et al. relates to a process for the direct crystallization of a pharmaceutical having high surface area particles of high purity and stability wherein impinging jet streams are employed to achieve high intensity micromixing of particles of the pharmaceutical followed by nucleation and direct production of small crystals.

A long-acting aripiprazole sterile injectionable formulation has merit as a drug dosage form in that it may increase the compliance of patients and thereby lower the rate of relapse in the treatment of schizophrenia. Examples of known long acting drug products for the treatment of schizophrenia include haloperidol decanoate and fluphenazine decanoate both of which have an ester compound of low water solubility dissolved in sesame oil. Microcapsules containing Risperidone (WO95/13814) and Olanzapine (WO99/12549) are also known.

BRIEF DESCRIPTION OF THE INVENTION

In accordance with the present invention, there is provided a sterile freeze-dried aripiprazole formulation which upon constitution with water for injection releases aripiprazole, in therapeutic amounts, over a period of at least about one week, and preferably over a period of two, three or four weeks and up to six weeks or more. The freeze-dried aripiprazole formulation of the invention includes:
(a) aripiprazole, and
(b) a vehicle for the aripiprazole,
which formulation upon constitution with water forms an injectable suspension which, upon injection, preferably intramuscularly, releases therapeutic amounts of aripiprazole over a period of at least one week, preferably two, three or four weeks, and up to six weeks or more.

The freeze-dried aripiprazole formulation of the invention will preferably include:
(a) aripiprazole,
(b) one or more suspending agents,
(c) optionally one or more bulking agents,
(d) optionally one or more buffers, and
(e) optionally one or more pH adjusting agents.

A mean particle size of the freeze-dried aripiprazole formulation within the range from about 1 to about 30 microns is essential in formulating an injectable which releases aripiprazole over a period of at least about one week and up to six weeks or more, for example up to 8 weeks.

It has been found that the smaller the mean particle size of the freeze-dried aripiprazole, the shorter the period of extended release. Thus, in accordance with the present invention, when the mean particle size is about 1 micron, the aripiprazole will be released over a period of less than three weeks, preferably about two weeks. When the mean particle size is more than about 1 micron, the aripiprazole will be released over a period of at least two weeks, preferably about three to four weeks, and up to six weeks or more. Thus, in accordance with the present invention, the aripiprazole release duration can be modified by changing the particle size of the aripiprazole in the freeze-dried formation.

The term "mean particle size" refers to volume mean diameter as measured by laser-light scattering (LLS) methods. Particle size distribution is measured by LLS methods and mean particle size is calculated from the particle size distribution.

In addition, in accordance with the present invention, a controlled release sterile injectable aripiprazole formulation in the form of a sterile suspension, that is, the freeze-dried formulation of the invention suspended in water for injection, is provided which, upon injection, preferably intramuscularly, releases therapeutic amounts of aripiprazole over a period of at least one week, which includes:
(a) aripiprazole,
(b) a vehicle therefor, and
(c) water for injection.

The controlled release sterile injectable formulation of the invention in the form of a sterile suspension allows for high drug loadings per unit volume of the formulation and therefore permits delivery of relatively high doses of aripiprazole in a small injection volume (0.1-600 mg of drug per 1 mL of suspension).

Further, in accordance with the present invention, a method is provided for preparing the sterile freeze-dried aripiprazole formulation described above which includes the steps of:

(a) preparing sterile bulk aripiprazole, preferably having a desired particle size distribution and mean particle size within the range from about 5 to about 100 microns, (b) preparing a sterile vehicle for the sterile bulk aripiprazole, (c) combining the sterile bulk aripiprazole and the sterile vehicle to form a sterile primary suspension, (d) reducing the mean particle size of aripiprazole in the sterile primary suspension to within the range from about 1 to about 30 microns, to form a final sterile suspension, and (e) freeze drying the final sterile suspension to form a sterile freeze-dried suspension of the aripiprazole of desired polymorphic form (anhydrous, monohydrate, or a mixture of both).

In carrying out the above method, the reduction of the mean particle size of the sterile primary suspension to the desired mean particle size is carried out employing an aseptic wet milling procedure, which preferably is aseptic wet ball milling. Aseptic wet milling is essential in forming a homogeneous and sterile aripiprazole formulation of desired mean particle size distribution.

In addition, in accordance with the present invention, a method for freeze drying the final sterile suspension of aripiprazole is provided which produces a sterile freeze-dried aripiprazole of desired polymorphic form, that is anhydrous, monohydrate, or a mixture of both.

Still further in accordance with the present invention, a method is provided for treating schizophrenia and related diseases which includes the step of administering to a patient in need of treatment therapeutic amounts of the above described controlled release injectable aripiprazole formulation.

As an unexpected observation, it has been discovered that a suspension of aripiprazole suspended in an aqueous solvent system will maintain a substantially constant aripiprazole drug plasma concentration when administered by injection; preferably as an intra-muscular injection. No large "burst phenomenon" is observed and it is considerably surprising that a constant aripiprazole drug plasma concentration can be maintained from one (1) to more than eight (8) weeks employing the aripiprazole suspension of the invention. The daily starting dose for an orally administered aripiprazole formulation is fifteen (15) milligrams. In order to administer a drug dose equivalent to one (1) to more than eight (8) weeks of the oral dosage quantity requires the administration of a very large amount of the drug as a single dose. The aqueous aripiprazole injectable formulation of the invention may be administered to deliver, large amounts of the drug without creating patient compliance problems.

The aripiprazole injectable formulation of the invention may include anhydrous or monohydrate crystalline forms of aripiprazole or an admixture containing both. If the monohydrate is used, the maintenance of an extended drug plasma concentration is possible.

The aripiprazole injectable formulation of the invention can be administered as an aqueous ready-to-use suspension; however, by freeze-drying this suspension a more useful drug product can be supplied.

DETAILED DESCRIPTION OF THE INVENTION

Figure 1:
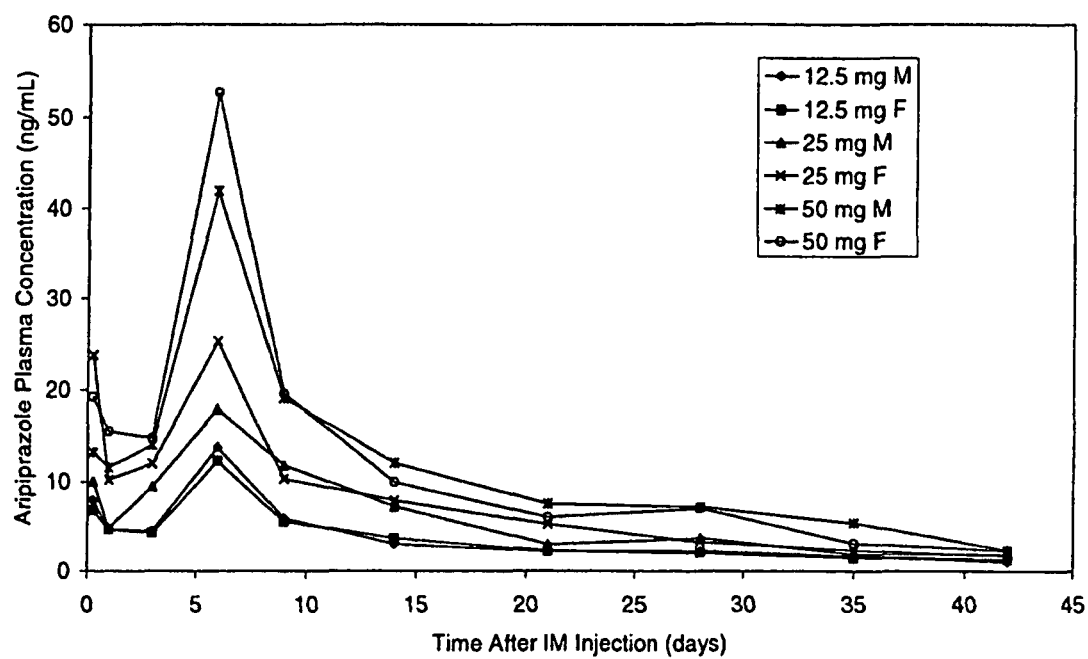
FIG. 1 is a graph depicting mean plasma concentrations versus time profiles of the Example 1 formulation of the invention in rats.

The controlled release sterile injectable aripiprazole formulation of the invention will include aripiprazole in an amount within the range from about 1 to about 40%, preferably from about 5 to about 20%, and more preferably from about 8 to about 15% by weight based on the weight of the sterile injectable formulation.

As indicated, desired mean particle size of the aripiprazole is essential in producing an injectable formulation having the desired controlled release properties of the aripiprazole. Thus, to produce desired controlled release, the aripiprazole should have a mean particle size within the range from about 1 to about 30 microns, preferably from about 1 to about 20 microns, and more preferably for about 1 to about 10 to 15 microns.

Where the desired controlled release period is at least about two weeks, up to six weeks or more, preferably about three to about four weeks, the aripiprazole will have a mean particle size within the range from about 1 to about 20, preferably from about 1 to about 10 microns, more preferably from about 2 to about 4 microns, and most preferably about 2.5 microns. The aripiprazole having a mean particle size of about 2.5 microns will have a particle size distribution as follows:

| Preferred | More Preferred |
| --- | --- |
| 95% < 20 microns | 95% < 8 microns |
| 90% < 15 microns | 90% < 6 microns |
| 50% < 10 microns | 75% < 3 microns |
| 10% < 2 microns | 50% < 1.5 microns |
|  | 10% < 0.5 microns |

The aripiprazole formulation of the invention will preferably be formed of:

A. aripiprazole,

B. a vehicle therefor, which includes:
(a) one or more suspending agents,
(b) one or more bulking agents,
(c) one or more buffers, and
(d) optionally one or more pH adjusting agents.

The suspending agent will be present in an amount within the range from about 0.2 to about 10% by weight, preferably for about 0.5 to about 5% by weight based on the total weight of the sterile injectable formulation. Examples of suspending agents suitable for use include, but are not limited to, one, two or more of the following: sodium carboxymethyl cellulose, hydroxypropyl cellulose, carboxymethyl cellulose, hydroxypropylethyl cellulose, hydroxypropylmethyl cellulose, and polyvinylpyrrolidone, with sodium carboxymethyl cellulose and polyvinylpyrrolidone being preferred. Other suspending agents suitable for use in the vehicle for the aripiprazole include various polymers, low molecular weight oligomers, natural products, and surfactants, including nonionic and ionic surfactants, such as cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxs 3350® and 1450®, and Carbopol 934® (Union Carbide)), dodecyl trimethyl ammonium bromide, polyoxyethylene stearates, collodial silicon dioxide, phosphates, sodium dodecylsulfate, carboxymethylcellulose ti calcium, hydroxypropyl celluloses (e.g., HPC, HPC-SL, and HPC-L), methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, dioctylsulfosuccinate (DOSS); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-1100, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); and SA9OHCO, which is $C_{18}H_{37}CH_2(CON(CH_3))$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-nonyl β-D-glucopyranoside; octanoyl-N-methylglucamide; n-octyl-β-D-glucopyranoside; octyl β-D-thioglucopyranoside; and the like.

Most of these suspending agents are known pharmaceutical excipients and are described in detail in the *Handbook of Pharmaceutical Excipients*, published jointly by the American Pharmaceutical Association and The Pharmaceutical Society of Great Britain (The Pharmaceutical Society of Great Britain (The Pharmaceutical Press, 1986), specifically incorporated by reference. The suspending agents are commercially available and/or can be prepared by techniques known in the art.

Carboxymethyl cellulose or the sodium salt thereof is particularly preferred where the desired mean particle size is about 1 micron or above.

The bulking agent (also referred to as a cryogenic/lyophilize protecting agent) will be present in an amount within the range from about 1 to about 10% by weight, preferably from about 3 to about 8% by weight, more preferably from about 4 to about 5% by weight based on the total weight of the sterile injectable formulation. Examples of bulking agents suitable for use herein include, but are not limited to, one, two or more of the following: mannitol, sucrose, maltose, xylitol, glucose, starches, sorbital, and the like, with mannitol being preferred for formulations where the mean particle size is about 1 micron or above. It has been found that xylitol and/or sorbitol enhances stability of the aripiprazole formulation by inhibiting crystal growth and agglomeration of drug particles so that desired particle size may be achieved and maintained.

The buffer will be employed in an amount to adjust pH of an aqueous suspension of the freeze-dried aripiprazole formulation to from about 6 to about 8, preferably about 7. To achieve such pH, usually the buffer, depending on type, will be employed in an amount within the range from about 0.02 to about 2% by weight, preferably from about 0.03 to about 1% by weight, and more preferably about 0.1% by weight based on the total weight of the sterile injectable formulation. Examples of buffers suitable for use herein include, but are not limited to, one, two or more of the following: sodium phosphate, potassium phosphate, or TRIS buffer, with sodium phosphate being preferred.

The freeze-dried formulation of the invention may optionally include a pH adjusting agent which is employed in an amount to adjust pH of the aqueous suspension of the freeze-dried aripiprazole within the range from about 6 to about 7.5, preferably about 7 and may be an acid or base depending upon whether the pH of the aqueous suspension of the freeze-dried aripiprazole needs to be raised or lowered to reach the desired neutral pH of about 7. Thus, where the pH needs to be lowered, an acidic pH adjusting agent which as hydrochloric acid or acetic acid, preferably hydrochloric acid, may be employed. When the pH needs to be raised, a basic pH adjusting agent will be employed such as sodium hydroxide, potassium hydroxide, calcium carbonate, magnesium oxide or magnesium hydroxide, preferably sodium hydroxide.

The freeze-dried aripiprazole formulations may be constituted with an amount of water for injection to provide from about 10 to about 400 mg of aripiprazole delivered in a volume of 2.5 mL or less, preferably 2 mL for a two to six week dosage.

In carrying out the method for preparing the freeze-dried aripiprazole formulation of the invention, it is required that everything be sterile so that sterile aripiprazole and sterile vehicle are combined aseptically to form a sterile suspension and that the sterile suspension be freeze-dried in a manner to form sterile freeze-dried powder or cake. Thus, an aseptic procedure is employed to produce sterile bulk aripiprazole of desired particle size distribution. The sterile bulk aripiprazole will have a mean particle size within the range from about 5 to about 100 microns, preferably from about 10 to about 90 microns.

Preferably, an impinging jet crystallization method is employed to produce sterile aripiprazole of desired small particle size and a narrow size distribution, high surface area, high chemical purity, high stability due to improved crystal structure, while employing continuous processing.

The impinging jet crystallization utilizes two jet streams that strike each other head-on. One of the streams carries a solution rich in the aripiprazole and the other carries an anti-solvent, such as water. The two streams strike each other which allows rapid homogeneous mixing and supersaturation due to high turbulence and high intensity of micromixing upon impact. This immediate achievement of supersaturation initiates rapid nucleation. In general, the average crystal size decreases with increasing supersaturation and decreasing temperature of the anti-solvent. Therefore, in order to obtain the smallest particle size, it is advantageous to have the highest possible concentration of the rich solution and the lowest temperature of the anti-solvent.

The vehicle for the sterile bulk aripiprazole including suspending agent, bulking agent, buffer, optional pH adjusting agent and water is prepared and subjected to sterilization.

Thereafter, the sterile bulk aripiprazole and sterile vehicle are aseptically combined to form a sterile primary suspension and the particle size of the aripiprazole is reduced to a desired level. This is preferably carried out employing an aseptic wet milling procedure wherein sterile particles of aripiprazole dispersed in the sterile vehicle are subjected to grinding means in the presence of grinding media to reduce the particle size of the aripiprazole to within the range of about 1 to about 10 microns, depending upon desired controlled release period.

The aseptic wet milling procedure is preferably wet ball milling. When the desired mean particle size of the aripiprazole is above about 1 micron, the primary suspension (combined aripiprazole-vehicle) is passed through a wet ball mill a single time (single pass) at from about 5 to about 15 L/hr, preferably from about 8 to about 12 L/hr, and more preferably about 10 L/hr, to reduce mean particle size of the aripiprazole to within the desired range, for example, from about 1 to about 5 microns.

In addition to ball mills, such as Dyno mills, other low and high energy mills may be employed such as a roller mill, and high energy mills may be employed such as Netzsch mills, DC mills and Planetary mills. However, it is essential that the milling procedure and equipment employed be capable of producing sterile aripiprazole formulation of desired mean particle size.

Other techniques for particle size reduction which may be employed include aseptic controlled crystallization, high shear homogenization, high pressure homogenization and microfluidization to produce particles having a mean particle size ranging from about 1 to about 100 microns.

The resulting final suspension is aseptically filled into sterile vials and aseptically loaded into a sterilized freeze drier. It is essential that a carefully designed freeze drying cycle be applied in order to form and/or maintain the desired crystalline form of the aripiprazole, which is known to exist in monohydrate form (Aripiprazole Hydrate A) as well as in a number of anhydrous forms, namely Anhydride Crystals B, Anhydride Crystals C, Anhydride Crystals D, Anhydride Crystals E, Anhydride Crystals F, and Anhydride Crystals G, all of which may be employed in the formulation of the invention.

The aripiprazole monohydrate (grains) or hydrate as referred to below employed in the present invention has the physicochemical properties given in (1)-(5) below. This aripiprazole hydrate is described hereinafter as "Aripiprazole Hydrate A".

(1) It has an endothermic curve characterized by the appearance of a small peak at about 71° C. and a gradual endothermic peak around 60° C. to 120° C.

(2) It has an $^1$H-NMR spectrum which has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

(3) It has a powder x-ray diffraction spectrum which has characteristic peaks at 2θ=12.6°, 15.4°, 17.3°, 18.0°, 18.6°, 22.5° and 24.8°.

(4) It has clear infrared absorption bands at 2951, 2822, 1692, 1577, 1447, 1378, 1187, 963 and 784 cm$^{-1}$ on the IR (KBr) spectrum.

(5) It has a mean grain size of 50 µm or less.

Aripiprazole Hydrate A is manufactured by milling conventional aripiprazole hydrate.

Conventional milling methods can be used to mill the aripiprazole hydrate. For example, the aripiprazole hydrate can be milled in a milling machine. A widely used milling machine can be used, such as an atomizer, pin mill, jet mill or ball mill. Of these, the atomizer is preferred.

Regarding the specific milling conditions when using an atomizer, a rotational speed of 5000-15000 rpm could be used for the main axis, for example, with a feed rotation of 10-30 rpm and a screen hole size of 1-5 mm.

The mean grain size of the Aripiprazole Hydrate A obtained by milling should normally be 50 µm or less, preferably 30 µm or less. Mean grain size can be ascertained by the grain size measurement method described hereinafter.

Grain Size Measurement: 0.1 g of the grains to be measured were suspended in a 20 ml n-hexane solution of 0.5 g soy lecithin, and grain size was measured using a size distribution meter (Microtrack HRA, Microtrack Co.).

The aripiprazole anhydride crystals employed in the present invention have the physicochemical properties given in (6)-(10) below. These aripiprazole anhydride crystals are referred to hereinafter as "Aripiprazole Anhydride Crystals B".

(6) They have an $^1$H-NMR spectrum which is substantially the same as the $^1$H-NMR spectrum (DMSO-d$_6$, TMS). Specifically, they have characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

(7) They have a powder x-ray diffraction spectrum which is substantially the same as the powder x-ray diffraction spectrum. Specifically, they have characteristic peaks at 2θ=11.0°, 16.6°, 19.3°, 20.3° and 22.1°.

(8) They have clear infrared absorption bands at 2945, 2812, 1678, 1627, 1448, 1377, 1173, 960 and 779 cm$^{-1}$ on the IR (KBr) spectrum.

(9) They exhibit an endothermic peak near about 141.5° C. in thermo-gravimetric/differential thermal analysis (heating rate 5° C./min).

(10) They exhibit an endothermic peak near about 140.7° C. in differential scanning calorimetry (heating rate 5° C./min).

Aripiprazole Anhydride Crystals B employed in the present invention have low hygroscopicity. For example, Aripiprazole Anhydride Crystals B employed in the present invention maintain a water content of 0.4% or less after 24 hours inside a dessicator set at a temperature of 60° C. and a humidity of 100%.

Well-known methods of measuring water content can be used as long as they are methods commonly used for measuring the water content of crystals. For example, a method such as the Karl Fischer method can be used.

The Aripiprazole Anhydride Crystals B employed in the present invention are prepared for example by heating the aforementioned Aripiprazole Hydrate A at 90-125° C. The heating time is generally about 3-50 hours, depending on heating temperature. The heating time and heating temperature are inversely related, so that for example the heating time will be longer the lower the heating temperature, and shorter the higher the heating temperature. Specifically, if the heating temperature of Aripiprazole Hydrate A is 100° C., the heating time should normally be 18 hours or more or preferably about 24 hours. If the heating temperature of Aripiprazole Hydrate A is 120° C., on the other hand, the heating time can be about 3 hours. The Aripiprazole Anhydride Crystals B of the present invention can be prepared with certainty by heating Aripiprazole Hydrate A for about 18 hours at 100° C., and then heating it for about 3 hours at 120° C.

Furthermore, the Aripiprazole Anhydride Crystals B employed in the present invention are prepared for example by heating conventional aripiprazole anhydride crystals at 90-125° C. The heating time is generally about 3-50 hours, depending on heating temperature. The heating time and heating temperature are inversely related, as described above. Specifically, if the heating temperature of the aripiprazole anhydride crystals is 100° C., the heating time can be about 4 hours, and if the heating temperature is 120° C. the heating time can be about 3 hours.

The aripiprazole anhydride crystals which are the raw material for preparing the Aripiprazole Anhydride Crystals B employed in the present invention are prepared for example by Method a or b below.

Method a:

Aripiprazole Anhydride Crystals B are prepared by well-known methods, as by reacting 7-(4-bromobutoxy)-3,4-dihydrocarbostyril with 1-(2,3-dichlorophenyl) piperidine and recrystallizing the resulting raw aripiprazole crystals with ethanol as described in Example 1 of Japanese Unexamined Patent Publication No. 191256/1990.

Method b:

Aripirazole Anhydride Crystals B are prepared by heating conventional aripiprazole hydrate at a temperature of at least 60° C. and less than 90° C. The heating time is generally about 1-30 hours, depending on heating temperature. The heating time and heating temperature are inversely related, as described above. Specifically, if the heating temperature of the aripiprazole hydrate is about 60° C., the heating time can be about 8 hours, while if the heating temperature is 80° C., the heating time can be about 4 hours.

Method b is described in the Proceedings of the 4th Japanese-Korean Symposium on Separation Technology (Oct. 6-8, 1996).

Furthermore, the Aripiprazole Anhydride Crystals B employed in the present invention are prepared for example by heating conventional aripiprazole hydrate at 90-125° C. The heating time is generally about 3-50 hours, depending on heating temperature. The heating time and heating temperature are inversely related. Specifically, if the heating temperature of the aripiprazole hydrate is 100° C., the heating time can be about 24 hours, while if the heating temperature is 120° C., the heating time can be about 3 hours.

The aripiprazole hydrate which is the raw material for preparing the Aripiprazole Anhydride Crystals B employed in the present invention is prepared for example by Method c below.

Method c:

Aripiprazole hydrate is obtained by dissolving the aripiprazole anhydride crystals obtained by Method a above in a hydrous solvent, and heating and then cooling the resulting solution. Using this method, aripiprazole hydrate is precipitated as crystals in the hydrous solvent.

An organic solvent containing water is usually used as the hydrous solvent. The organic solvent should be one which is miscible with water, such as for example an alcohol such as methanol, ethanol, propanol or isopropanol, a ketone such as acetone, an ether such as tetrahydrofuran, dimethylformamide, or a mixture thereof, with ethanol being particularly desirable. The amount of water in the hydrous solvent can be 10-25% by weight of the solvent, or preferably close to 20% by weight.

As mentioned above, the Aripiprazole Anhydride Crystals B employed in the present invention are prepared by heating at 90-125° C. of the Aripiprazole Hydrate A, conventional aripiprazole anhydride crystals or conventional aripiprazole hydrate, and the Aripiprazole Hydrate A, conventional aripiprazole anhydride crystals or conventional aripiprazole hydrate may be used either individually or in combination.

The above crystal forms and other crystal forms of aripiprazole and methods for making such crystal forms which may be employed herein include Hydrate A and Anhydride Crystals B as well as Anhydride Crystals C, Anhydride Crystals D, Anhydride Crystals E, Anhydride Crystals F, and Anhydride Crystals G, as disclosed in PCT WO 03/26659, published Apr. 4, 2003.

If the monohydrate form of the aripiprazole in the freeze-dried formulation is desired then the freeze drying cycle should include cooling of the formulation to about −40° C. at a suitable cooling rate. The primary drying should be performed at a temperature below around 0° C. and a suitable vacuum and duration.

If the anhydrous form of the aripiprazole in the freeze-dried formulation is desired then the freeze drying cycle should include three phases: freezing, primary drying, and secondary drying. The freezing phase should include cooling of the formulation to about −40° C. at a suitable cooling rate. The primary drying should be performed at a temperature below about 0° C. and a suitable vacuum and duration. The secondary drying should be performed at a temperature above about 0° C. and a suitable vacuum and duration.

The vials with the resulting freeze-dried aripiprazole suspension are aseptically stoppered under atmospheric pressure or partial vacuum and sealed.

Preferred injectable formulations in the form of aqueous suspensions are set out below:

| Preferred Particle Size of About 1-10 Microns (Preferably About 2.5 Microns) | | |
|---|---|---|
| | Range % w/v | Preferred Range % w/v |
| (1) Sterile Aripiprazole - (mean particle size from about 1 to about 5 microns) | 1 to 40 | 8 to 15 |
| (2) Suspending Agent (preferably carboxymethyl cellulose Na salt) | 0.2 to 10 | 0.5 to 5 |
| (3) Bulking Agent (preferably mannitol) | 1 to 10 | 4 to 5 |
| (4) Buffer (preferably sodium phosphate) (adjust pH to about 6 to about 7.5) | 0.02 to 2 | 0.03 to 1 |
| (5) pH Adjusting Agent (preferably sodium hydroxide) (adjust pH to about 6 to about 7.5) | As needed | As needed |
| (6) Water for injection | As needed | As needed |

The aripiprazole will be present in the aqueous injectable formulation in an amount within the range from about 1 to about 40% (w/v), preferably from about 5 to about 20% (w/v), and more preferably from about 8 to about 15% (w/v), based on the total injectable formulation.

In preferred embodiments, the aripiprazole will be present in the aqueous injectable formulation to provide from about 50 to about 400 mg/2 mL of formulation, preferably from about 100 to about 200 mg/mL of formulation.

Preferred individual dose injectable formulations in accordance with the invention are as follows:

| aripiprazole | 100 mg | 200 mg | 400 mg |
|---|---|---|---|
| carboxymethyl cellulose | 9 mg | 9 mg | 9 mg |
| mannitol | 45 mg | 45 mg | 45 mg |
| Na phosphate | 0.8 mg | 0.8 mg | 0.8 mg |
| sodium hydroxide | qs to adjust pH to 7 | qs to adjust pH to 7 | qs to adjust pH to 7 |
| water for injection | qs to 1 mL | qs to 1 mL | qs to 1 mL |

The aripiprazole formulations of the invention are used to treat schizophrenia and related disorders such as bipolar disorder and dementia in human patients. The preferred dosage employed for the injectable formulations of the invention will be a single injection or multiple injections containing from about 100 to about 400 mg aripiprazole/mL given one to two times monthly. The injectable formulation is preferably administered intramuscularly, although subcutaneous injections are acceptable as well.

The following examples represent preferred embodiments of the invention.

EXAMPLES

Example 1

An aripiprazole injectable (IM Depot) aqueous suspension (200 mg aripiprazole/2 mL, 200 mg/vial) was prepared as follows.

Aripiprazole Microsuspension Prepared by Media Milling

A microparticulate dispersion of aripiprazole was prepared using a DYNO®-MILL (Type KDL A, manufactured by Willy A. Bachoffen AG Maschinenfabrik, Basel, Switzerland).

The following ingredients were added to a 3 L glass jacketed vessel maintained at 15° C. (±5° C.) to form a sterile primary suspension:

| Aripiprazole | 100 g |
|---|---|
| Carboxymethylcellulose, Sodium Salt 7L2P | 9.0 g |
| Mannitol | 45 g |
| Sodium Phosphate, Monobasic | 0.8 g |
| Sodium Hydroxide Solution, 1N | q.s. to adjust pH to 7.0 |
| Water for Injection, USP | q.s. to 1040 g |

The primary suspension was mixed at 500-1000 rpm for about 0.5 hour and then at 300-500 rpm for an additional 1 hour under 20"Hg (±5"Hg) vacuum.

The media mill was prepared accordingly for the media milling process. The grinding container was partially filled with zirconium oxide beads and the dispersion was passed through the mill operating at the following conditions:

| Grinding container: | water jacketed 0.6 L stainless steel vessel |
|---|---|
| Coolant temperature: | 15° C. (±5° C.) |
| Agitation speed: | 2500 rpm |
| Grinding medium: | 500 mL of very-high-density (VHD) zirconium oxide beads |

-continued

| Suspension flow rate: | 10 L/h |
|---|---|
| Milling time: | 6 minutes |

After a single pass milling, a sample of the processed suspension was removed and evaluated for particle size distribution using Horiba LA-910 Laser Scattering Particle Size Distribution Analyzer. The particles were determined to have a mean particle size of 2.5 microns (μ) and the following particle size distribution: 10%<0.4μ, 50%<1.6μ, 75%<3.3μ, 90%<5.9μ, and 95%<7.6μ.

2.5 mL of the above suspension were aseptically filled into sterilized vials which were then aseptically partially stoppered with sterilized stoppers. The vials were aseptically transferred to a freeze dryer and lyophilized according to the following cycle:

(a) thermal treatment: freeze product at −40° C. over 0.1-1 h and keep at −40° C. for at least 3 h, (b) cool the condenser to −50° C. or below, (c) primary drying: lower chamber pressure to approximately 100 microns Hg and increase product temperature to −5° C. over approximately 2 h; continue primary drying at −5° C. and 100 microns Hg for at least 48 h, (d) stopper the vials under atmospheric pressure or partial vacuum using sterile nitrogen or air and remove from the freeze dryer, (e) seal the vials with the appropriate seals and label.

Example 2

An aripiprazole injectable (IM Depot) aqueous suspension (200 mg aripiprazole/2 mL, 200 mg/vial) was prepared as follows.

Aripiprazole Microsuspension Prepared by Impinging Jet Crystallization

A microparticulate dispersion of aripiprazole was prepared using impinging jet crystallization.

The following procedure was employed to form a sterile bulk aripiprazole:

1. Suspend 100 g of aripiprazole in 2000 mL of 95% ethanol. Heat the suspension to 80° C. until it becomes a clear solution.

2. Polish filter the aripiprazole solution into a holding vessel and maintain at 80° C.

3. Polish filter 2000 mL water to another holding vessel and heat to 80° C.

4. Pump the aripiprazole solution through a 0.02 inch diameter nozzle at 0.25 kg/min and impinge it with the 30° C. water pumped at 0.25 kg/min through a 0.02 inch diameter nozzle to form a crystal slurry which is collected in an impingement vessel.

5. Agitate the newly formed crystal slurry in the impingement vessel while continuously transferring it to a receiver to maintain a constant volume in the impingement vessel.

6. At the end of impingement, cool the slurry in the receiver to room temperature.

7. Filter the slurry.

8. Dry the wet cake at 35° C. under vacuum to yielding 100 g (96% recovery) of aripiprazole with reduced particle size (90%<100 μm).

The following ingredients were added to a 3 L glass jacketed vessel maintained at 15° C. (±5° C.) to form a sterile primary suspension:

| | |
|---|---|
| Aripiprazole (prepared by impinging jet crystallization): | 100 g |
| Carboxymethylcellulose, Sodium Salt 7L2P | 9.0 g |
| Mannitol | 45 g |
| Sodium Phosphate, Monobasic | 0.8 g |
| Sodium Hydroxide Solution, 1N | q.s. to adjust pH to 7.0 |
| Water, USP | q.s. to 1040 g |

The sterile suspension was mixed at 500-1000 rpm for about 0.5 hour and then at 300-500 rpm for an additional 1 hour under 20"Hg (±5"Hg) vacuum.

The sterile suspension was found to contain particles having mean particle size of 2.5 microns and the following particle size distribution:

| | |
|---|---|
| 10% | < 0.4µ |
| 50% | < 1.6µ |
| 75% | < 3.3µ |
| 90% | < 5.9µ |
| 95% | < 7.5µ |

2.5 mL of the above suspension were aseptically filled into sterilized vials which were then aseptically partially stoppered with sterilized stoppers. The vials were aseptically transferred to a freeze dryer and lyophilized according to the following cycle:

(a) thermal treatment: freeze product at −40° C. over 0.1-1 h and keep at −40° C. for at least 6 h, (b) cool the condenser to −50° C. or below, (c) primary drying: lower chamber pressure to approximately 100 microns Hg and increase product temperature to −5° C. over approximately 2 h; continue primary drying at −5° C. and 100 microns Hg for at least 48 h, (d) stopper the vials under atmospheric pressure or partial vacuum using sterile nitrogen or air and remove from the freeze dryer, (e) seal the vials with the appropriate seals and label.

Example 3

Animal PK Data

A. Single-Dose I.M. Depot Study in Rats

Aripiprazole I.M. depot formulation prepared in Example 1 was injected into the thigh muscle of fifteen rats (M-males, F-females) at doses of 12.5, 25, and 50 mg/kg. Blood samples for the evaluation of systemic exposure after aripiprazole I.M. depot administration were collected on days 1 (6 h postdose), 2, 4, 7, 10, 15, 22, 28, 36, and 43 and analyzed for aripiprazole. FIG. 1 shows mean plasma concentrations vs. time profiles of aripiprazole in rats.

B. Single-Dose I.M. Depot Study in Dogs

Figure 2:
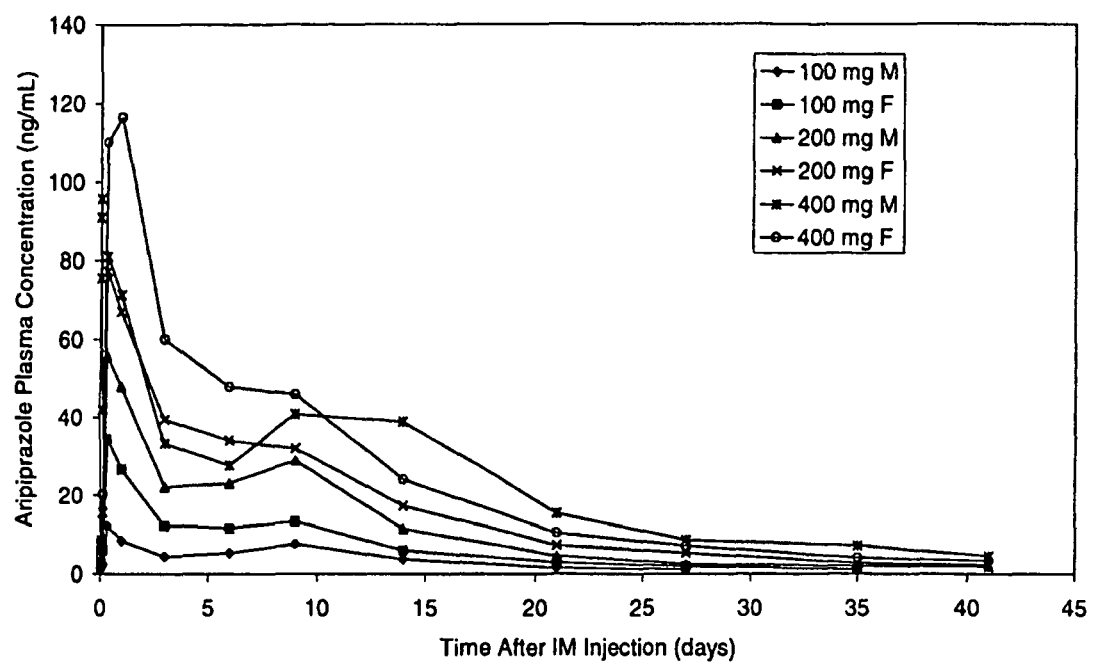
FIG. 2 is a graph depicting mean plasma concentrations versus time profiles of the Example 1 formulation of the invention in dogs.

The aripiprazole intramuscular (I.M). depot formulation prepared in Example 1 was injected into the thigh muscle of five dogs (M-males, F-females) at doses of 100, 200, and 400 mg. Blood samples for the evaluation of systemic exposure after aripiprazole I.M. depot administration were collected on days 1 (10 and 30 minutes, and 1, 3, and 8 h postdose), 2, 4, 7, 10, 15, 22, 28, 36, and 42 and analyzed for aripiprazole. FIG. 2 shows mean plasma concentrations vs. time profiles of aripiprazole in dogs.

PK Profiles

Mean aripiprazole rats' serum concentration-time profiles are shown graphically in FIG. 1. Aripiprazole aqueous suspensions showed steady serum concentration for at least 4 weeks in the rats' model.

Mean aripiprazole dogs' serum concentration-time profiles are shown graphically in FIG. 2.

Aripiprazole aqueous suspensions showed steady serum concentration for 3-4 weeks in the dogs' model.

Example 4

Human PK Data

Single-Dose I.M. Depot Study in Patients

Aripiprazole I.M. depot formulation prepared in Example 1 was administered intramuscularly to patients diagnosed with chronic, stable schizophrenia or schizoaffective disorder at. The study design included administration of a 5-mg dose of aripiprazole solution to all subjects followed by a single dose of IM depot at 15, 50, and 100 mg per patient. Samples for PK analysis were collected until plasma concentrations of aripiprazole were less than the lower limit of quantification (LLQ) for 2 consecutive visits.

Figure 3:
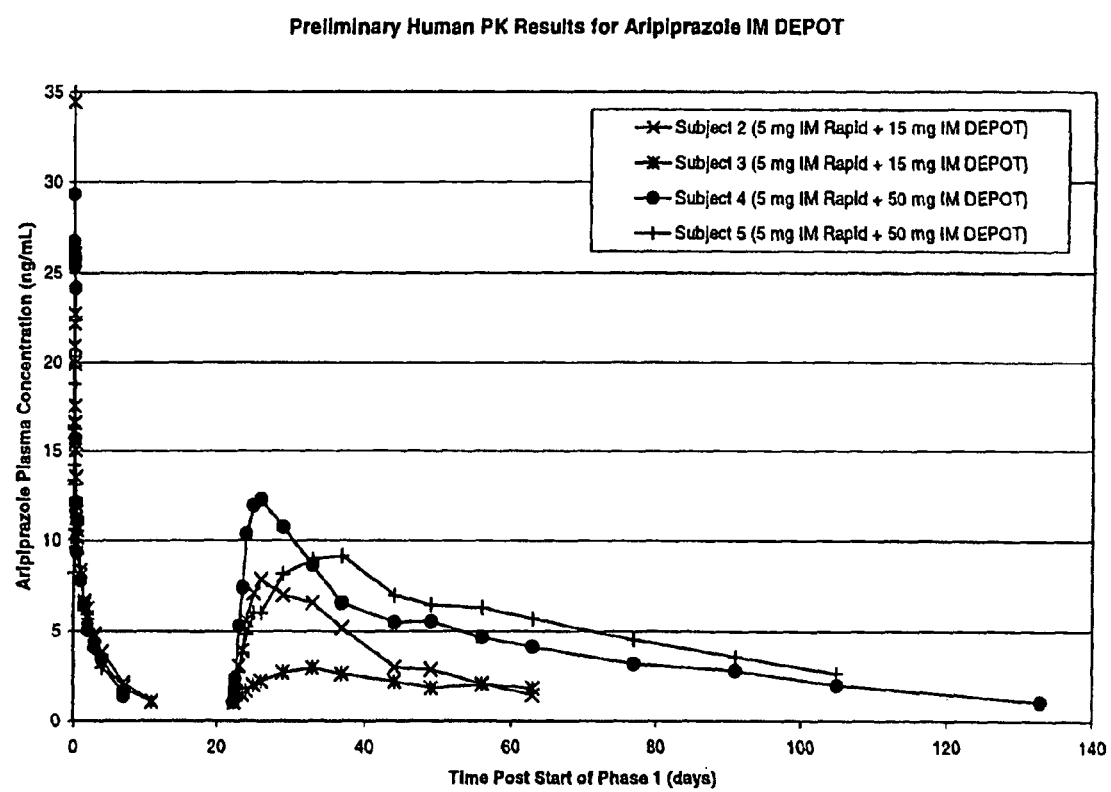
FIG. 3 is a graph depicting mean plasma concentrations vs. time profiles of the Example 1 formulation of the invention in humans.

FIG. 3 shows mean plasma concentrations vs. time profiles of aripiprazole in subjects 2 and 3 dosed with 15 mg of IM Depot, and subjects 4 and 5 who received 50 mg of IM Depot. In all cases aripiprazole plasma levels showed a fast onset of release and sustained release for at least 30 days.

What is claimed is:

1. A method of treating schizophrenia, which comprises administering to a subject in need of treatment thereof, a sterile injectable formulation obtained by reconstitution of a homogeneous suspension from a sterile freeze-dried controlled release aripiprazole formulation which comprises:

(a) aripiprazole having a mean particle size of about 1 to 10 microns, and (b) one or more suspending agents, wherein said sterile freeze-dried controlled release aripiprazole formulation is in the form of a cake obtained by freeze-drying a homogeneous aqueous suspension comprising (a) and (b), and wherein upon reconstitution, which comprises adding water to said cake, the sterile injectable formulation is obtained which is a homogeneous suspension and which contains from about 0.1 to about 600 mg of aripiprazole per mL, and wherein upon injection into a subject, said sterile injectable formulation releases aripiprazole over a period of at least about two weeks from the date of administration.

2. The method as defined in claim 1, wherein the sterile injectable formulation is administered intramuscularly or subcutaneously.

3. The method of treating schizophrenia as defined in claim 1, wherein the sterile freeze-dried controlled release aripiprazole formulation further comprises:

(c) one or more bulking agents, and (d) one or more buffering agents.

4. The method as defined in claim 3, wherein the sterile injectable formulation is administered intramuscularly or subcutaneously.

5. The method of treating schizophrenia as defined in claim 3, wherein the sterile freeze-dried controlled release aripiprazole formulation comprises:

(a) aripiprazole having a mean particle size of about 1 to 10 microns, (b) carboxymethyl cellulose or its sodium salt, (c) mannitol, (d) sodium phosphate to adjust pH to about 7, and
(e) optionally sodium hydroxide to adjust pH to about 7,
wherein upon injection into a subject, said sterile injectable formulation releases aripiprazole over a period of at least about three weeks from the date of administration.

6. The method as defined in claim 5, wherein the sterile injectable formulation is administered intramuscularly or subcutaneously.

7. A method of treating schizophrenia, which comprises administering to a subject in need of treatment thereof, a sterile injectable formulation obtained by reconstitution of a homogeneous suspension from a sterile freeze-dried controlled release aripiprazole formulation which comprises:
   (a) aripiprazole having a mean particle size of about 1 to 10 microns, and
   (b) one or more suspending agents,
wherein said freeze-dried formulation is in the form of a cake obtained by freeze-drying a homogeneous aqueous suspension comprising (a) and (b), and wherein upon reconstitution, which comprises adding water to said cake, the sterile injectable formulation is obtained which is a homogeneous suspension and which contains from about 0.1 to about 600 mg of aripiprazole per mL, and wherein upon injection into a subject, said sterile injectable formulation releases aripiprazole over a period of at least about one week from the date of administration.

8. The method as defined in claim 7, wherein the sterile injectable formulation is administered intramuscularly or subcutaneously.

9. The method as defined in claim 1, wherein the sterile injectable formulation comprises from 100 to 400 mg aripiprazole/mL and is administered one to two times monthly.

10. The method as defined in claim 3, wherein the sterile injectable formulation comprises from 100 to 400 mg aripiprazole/mL and is administered one to two times monthly.

11. The method as defined in claim 5, wherein the sterile injectable formulation comprises from 100 to 400 mg aripiprazole/mL and is administered one to two times monthly.

12. The method as defined in claim 7, wherein the sterile injectable formulation comprises from 100 to 400 mg aripiprazole/mL and is administered one to two times monthly.

13. The method as defined in claim 1, wherein the aripiprazole has a mean particle size of about 2 to about 4 microns.

14. The method as defined in claim 1, wherein the aripiprazole has a mean particle size of about 2.5 microns.

15. The method as defined in claim 1, wherein the aripiprazole is in the form of anhydrous crystals or in the form of a monohydrate.

16. The method as defined in claim 15, wherein the aripiprazole is in the form of Aripiprazole Anhydride Crystals B or Aripiprazole Hydrate A.

17. The method as defined in claim 3, wherein the aripiprazole is in the form of anhydrous crystals or in the form of a monohydrate.

18. The method as defined in claim 17, wherein the aripiprazole is in the form of Aripiprazole Anhydride Crystals B or Aripiprazole Hydrate A.

19. The method as defined in claim 5, wherein the aripiprazole is in the form of anhydrous crystals or in the form of a monohydrate.

20. The method as defined in claim 19, wherein the aripiprazole is in the form of Aripiprazole Anhydride Crystals B or Aripiprazole Hydrate A.

21. The method as defined in claim 3, wherein said sterile injectable formulation comprises:

(a) aripiprazole having a mean particle size of about 1 to about 10 microns in an amount within the range from about 1 to about 40%,
(b) suspending agent in an amount within the range from about 0.2 to about 10%,
(c) bulking agent in an amount within the range from about 1 to about 10%, and
(d) buffering agent in an amount within the range from about 0.02 to about 2% to adjust the pH of the sterile injectable formulation within the range from about 6 to about 7.5,
wherein all of the above % are % by weight/volume based on the volume of the sterile injectable formulation.

22. The method as defined in claim 3, wherein the suspending agent is selected from the group consisting of carboxymethylcellulose or its sodium salt, hydroxypropyl cellulose, hydroxypropylethyl cellulose, hydroxypropylmethyl cellulose, and polyvinylpyrrolidone; the bulking agent is selected from the group consisting of mannitol, sucrose, maltose, lactose, xylitol and sorbitol; and the buffering agent is selected from the group consisting of sodium phosphate, potassium phosphate and TRIS buffer.

23. The method as defined in claim 5, wherein the sterile injectable formulation is selected from the group consisting of the following Formulations A, B and C:

|  | Formulation A | Formulation B | Formulation C |
| --- | --- | --- | --- |
| aripiprazole having a mean particle size of about 1 to 10 microns | 100 mg | 200 mg | 400 mg |
| Carboxymethyl Cellulose | 9 mg | 9 mg | 9 mg |
| Mannitol | 45 mg | 45 mg | 45 mg |
| Sodium phosphate | 0.8 mg | 0.8 mg | 0.8 mg |
| Sodium Hydroxide | qs to adjust pH to 7 | qs to adjust pH to 7 | qs to adjust pH to 7 |
| Water for Injection | qs to 1 mL | qs to 1 mL | qs to 1 mL. |

24. The method as defined in claim 21, wherein the sterile injectable formulation comprises:
(a) aripiprazole having a mean particle size of about 1 to about 5 microns in an amount within the range from about 1 to about 40%,
(b) suspending agent in an amount within the range from about 0.2 to about 10%,
(c) bulking agent in an amount within the range from about 1 to about 10%, and
(d) buffering agent in an amount within the range from about 0.02 to about 2% to adjust the pH of the sterile injectable formulation to about 6 to about 7.5,
wherein all of the above % are % by weight/volume based on the total volume of the sterile injectable formulation.

25. The method as defined in claim 24, wherein the sterile injectable formulation comprises:
(a) aripiprazole having a mean particle size of about 2.5 microns in an amount within the range from about 5 to about 20%,
(b) suspending agent in an amount within the range from about 0.5 to about 5%,
(c) bulking agent in an amount within the range from about 4 to about 5%, and
(d) buffering agent in an amount within the range from about 0.03 to about 1% to adjust the pH of the sterile injectable formulation to about 6 to about 7.5, wherein all of the above % are % by weight/volume based on the total volume of the sterile injectable formulation.

26. The method as defined in claim 14, wherein the aripiprazole having a mean particle size of about 2.5 microns has a particle size distribution as follows:
95%<20 microns
90%<15 microns
50%<10 microns
10%<2 microns.

27. The method as defined in claim 25, wherein the aripiprazole having a mean particle size of about 2.5 microns has a particle size distribution as follows:
95%<20 microns
90%<15 microns
50%<10 microns
10%<2 microns.

28. The method as defined in claim 1, wherein the sterile injectable formulation contains from about 50 to about 400 mg of aripiprazole per 2 mL.

29. The method as defined in claim 1, wherein the sterile injectable formulation contains from about 100 to about 200 mg of aripiprazole per mL.

30. The method as defined in claim 3, wherein the sterile injectable formulation contains from about 50 to about 400 mg of aripiprazole per 2 mL.

31. The method as defined in claim 3, wherein the sterile injectable formulation contains from about 100 to about 200 mg of aripiprazole per mL.

32. The method as defined in claim 5, wherein the sterile injectable formulation contains from about 50 to about 400 mg of aripiprazole per 2 mL.

33. The method as defined in claim 5, wherein the sterile injectable formulation contains from about 100 to about 200 mg of aripiprazole per mL.

34. The method as defined in claim 7, wherein the sterile injectable formulation contains from about 50 to about 400 mg of aripiprazole per 2 mL.

35. The method as defined in claim 7, wherein the sterile injectable formulation contains from about 100 to about 200 mg of aripiprazole per mL.

\* \* \* \* \*

UNITED STATES PATENT AND TRADEMARK OFFICE
CERTIFICATE OF CORRECTION

| | |
|---|---|
| PATENT NO. | : 8,030,313 B2 |
| APPLICATION NO. | : 11/979149 |
| DATED | : October 4, 2011 |
| INVENTOR(S) | : Janusz W. Kostanski et al. |

It is certified that error appears in the above-identified patent and that said Letters Patent is hereby corrected as shown below:

On the Title Page, Item 56

Page 2, right column, lines 61-62

Change:

"Pharmaceutical Dosage Forms: Disperse Systems, vol. 1, pp. 153-163 (1998), Lieberman et al. eds., Marcel Dekker Inc."

To read:

--Pharmaceutical Dosage Forms: Disperse Systems, vol. 1, pp. 153-163 (1988), Lieberman et al. eds., Marcel Dekker Inc.--;

Page 3, left column, lines 7-9

Change:

""Prostein: Oxendolone Injectable Aqueous Suspension Formulation Extracts", Standard Commodity Classification No. of Japan 872499 (Jan. 1992)."

To read:

--"Prostetin: Oxendolone Injectable Aqueous Suspension Formulation Extracts", Standard Commodity Classification No. of Japan 872499 (Jan. 1992).--;

In the Specifications

Column 7, lines 38-40, delete each occurrence of "Anhydride" and insert --Anhydrous--;

Column 8, lines 18 and 20, delete "anhydride" and insert --anhydrous--;

Column 8, lines 21, 45, 47, 55 and 67, delete each occurrence of "Anhydride" and insert --Anhydrous--;

Column 9, line 4, delete "Anhydride" and insert --Anhydrous--;

Column 9, lines 6, 11 and 14, delete each occurrence of "anhydride" and insert --anhydrous--;

Signed and Sealed this
Fifteenth Day of April, 2014

Michelle K. Lee
*Deputy Director of the United States Patent and Trademark Office*

CERTIFICATE OF CORRECTION (continued)
U.S. Pat. No. 8,030,313 B2

Column 9, lines 15 and 19, delete "Anhydride" and insert --Anhydrous--;

Column 9, line 19, after "Crystals", delete "B";

Column 9, line 26, delete "Anhydride" and insert --Anhydrous--;

Column 9, line 26, after "Crystals", delete "B";

Column 9, lines 38 and 48, delete "Anhydride" and insert --Anhydrous--;

Column 9, line 53, delete "anhydride" and insert --anhydrous--;

Column 9, line 66, delete "Anhydride" and insert --Anhydrous--;

Column 10, lines 2 and 4, delete "anhydride" and insert --anhydrous--;

Column 10, lines 8-11, delete each occurrence of "Anhydride" and insert --Anhydrous--;

In the Claims

Column 15, lines 52, 58 and 64 (Claims 16, 18 and 20), delete "Anhydride" and insert --Anhydrous--.